United States Patent
Sugihara et al.

[11] Patent Number: 5,863,653
[45] Date of Patent: Jan. 26, 1999

[54] RAYON FIBER CONTAINING TOURMALINE PARTICLES AND METHOD FOR THE PREPARATION THEREOF

[75] Inventors: Toshio Sugihara; Mitsuo Suzuki; Marcos Masaki Komiya, all of Tokyo-to, Japan

[73] Assignee: Life Energy Industry Inc., Japan

[21] Appl. No.: 872,062

[22] Filed: Jun. 10, 1997

Related U.S. Application Data

[63] Continuation-in-part of Ser. No. 678,061, Jul. 9, 1996, Pat. No. 5,787,525.

[51] Int. Cl.$^6$ .................................................. D02G 3/00
[52] U.S. Cl. ............................................ 428/372; 428/393
[58] Field of Search ...................................... 428/372, 393

[56] References Cited

U.S. PATENT DOCUMENTS 5,601,909  2/1997  Kubo ........................................ 428/372

FOREIGN PATENT DOCUMENTS 6-104926  12/1994  Japan .

*Primary Examiner*—Newton Edwards
*Attorney, Agent, or Firm*—Wenderoth, Lind & Ponack, L.L.P.

[57] ABSTRACT

Proposed is an electret fiber which is a rayon fiber containing 0.05 to 2.0% by weight of tourmaline particles having a particle diameter not exceeding 0.3 μm. The electret fiber is effective for invigoration of human body by promoting blood circulation. The electret fiber is prepared by spinning a spinning solution of rayon containing the tourmaline particles uniformly dispersed therein into the form of a fiber.

11 Claims, 2 Drawing Sheets

RAYON FIBER CONTAINING TOURMALINE PARTICLES AND METHOD FOR THE PREPARATION THEREOF

This is a continuation-in-part application of U.S. patent application Ser. No. 08/678,061 filed Jul. 9, 1996, now U.S. Pat. No. 5,787,525.

BACKGROUND OF THE INVENTION

The present invention relates to a novel fibrous material which is a rayon fiber containing fine particles of tourmaline and to a method for the preparation thereof. More particularly, the invention relates to a rayon fiber capable of emitting active ions to exhibit an effect of invigoration or activation of living body cells as well as to a method for the preparation thereof.

It is an issue of interest in recent years that living body cells can be activated by so-called active ions to improve the healthful condition of the living body so that various studies are now under way to utilize active ions for the control of autonomic and motorial nervous systems, promotion of sound sleep, ataractic stabilization, acceleration of recovery from fatigue and so on.

As one of the substances which emit such active ions, tourmaline, which is a naturally occurring mineral but can be synthesized artificially, is proposed as promising. Namely, tourmaline is the strongest in the permanent spontaneous electric polarizability among known electret minerals having permanent polarizability so that the vector of polarization thereof is not influenced by an external electric field. It is also noted that the tourmaline mineral emits far-infrared light.

One of the inventors has proposed, directing his attention to these facts, tourmaline-containing electret fibers in Japanese Patent Publication 6-104926 after extensive investigations on the beneficial effects such as improvement of blood circulation on a person wearing clothes or athletic supporters made from a fabric of certain fibers containing fine particles of tourmaline.

SUMMARY OF THE INVENTION

The present invention accordingly has an object to provide a novel tourmaline-containing electret rayon-based fiber capable of emitting active ions in a greatly improved high efficiency and useful not only for the purpose of activation of living body cells as well as an efficient method for the preparation thereof.

Thus, the electret fiber provided by the invention is a fiber of rayon, which includes the rayon fibers of the viscose process and cuprammonium process, containing from 0.05 to 2.0% by weight or, preferably, from 0.05 to 0.5% by weight, based on the amount of the rayon, of particles of tourmaline having a particle diameter not exceeding 0.3 μm uniformly dispersed in the fiber.

The above defined rayon-based electret fiber of the invention is prepared by a method which comprises the steps of:

(a) preparing an aqueous spinning solution of rayon;

(b) uniformly dispersing particles of tourmaline having a particle diameter not exceeding 0.3 μm in the aqueous spinning solution in an amount in the range, preferably, from 0.05 to 2.0% by weight based on the amount of the rayon; and (c) spinning the tourmaline-containing spinning solution of rayon into the form of a tourmaline-containing fiber.

DETAILED DESCRIPTION OF THE PREFERRED EMBODIMENTS

Figure 1:
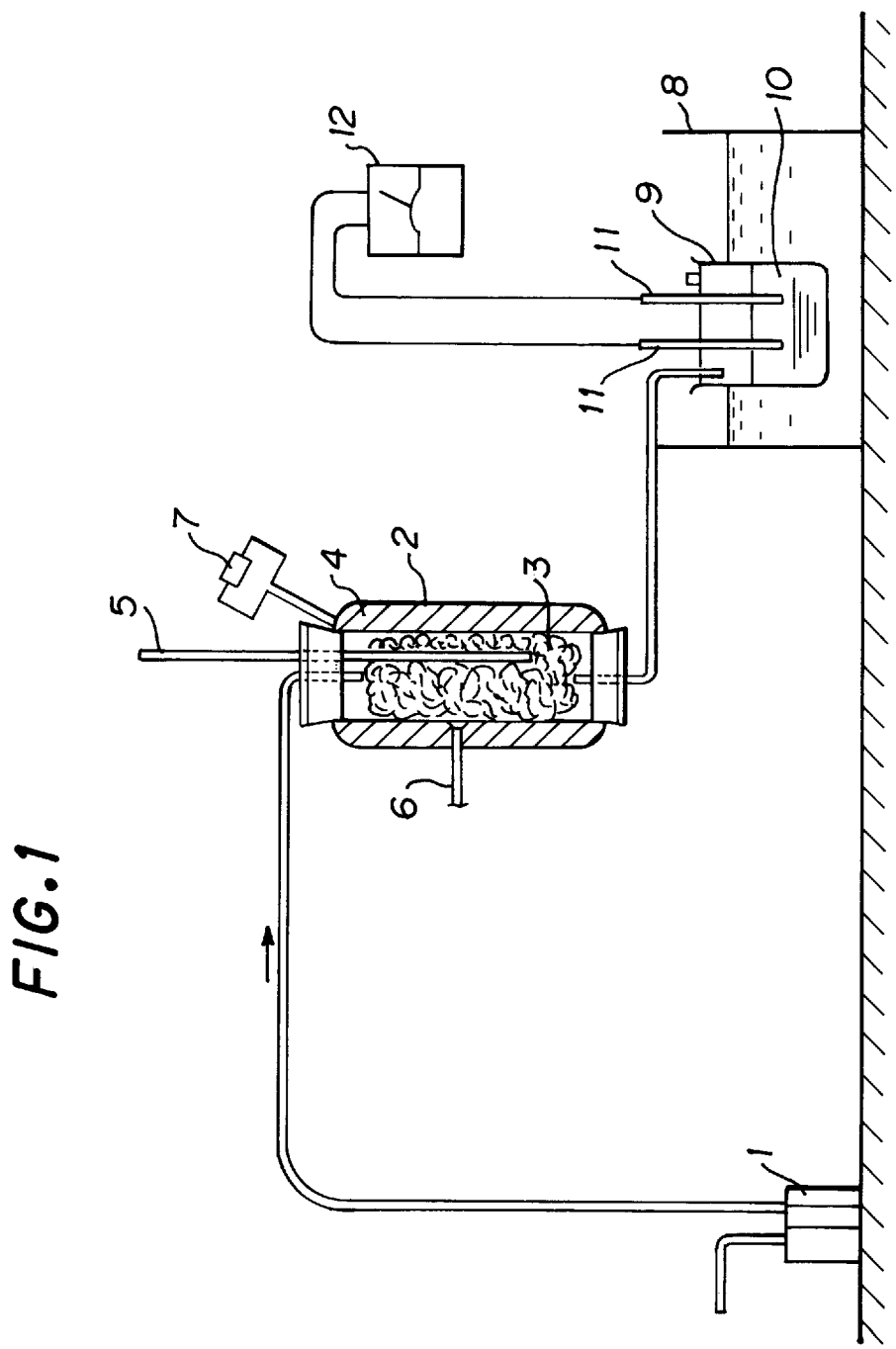
FIG. 1 is a schematic illustration of the system for the measurement of active ion emission from the electret fibers.

As is described above, the electret fiber of the invention is a rayon fiber containing particles of tourmaline having a specified particle size and uniformly dispersed in the fiber body in a specified amount.

Namely, the particles of tourmaline in the inventive electret fiber should have a particle diameter not exceeding 0.3 μm or, preferably, not exceeding 0.2 μm. The amount of the tourmaline particles dispersed in the rayon fiber is in the range from 0.05 to 2.0% or, preferably, 0.05 to 0.5% by weight based on the amount of the rayon fiber. When these requirements are satisfied, the tourmaline-containing rayon fibers of the invention are useful for the purpose of living body invigoration.

It is a quite unexpected discovery that the tourmaline particles having an extremely fine particle diameter as mentioned above can be easily and very uniformly dispersed in the spinning solution of rayon even without addition of a dispersion aid to the spinning solution so that a very high active ion-emitting efficiency can be obtained with a relatively low content of the tourmaline particles in the rayon fibers. This unexpected advantage with the extremely fine tourmaline particles is presumably a consequence of the fact that the cellulosic moiety in the spinning solution of rayon is a kind of polymeric electrolyte to exhibit strong interaction with the spontaneously polarized tourmaline particles.

Generally speaking, it is a trend in dispersing fine particles of a foreign material into a solution of a polymeric material as a spinning solution of fibers that an increased difficulty is encountered in accomplishing uniformity of the particle dispersion as the particle diameter of the particles is decreased due to formation of agglomerates of the primary particles. Accordingly, it is a usual practice in obtaining such a uniform dispersion that the dispersion is admixed with a dispersion aid which, however, is not quite effective when the particle diameter of the particles is extremely small. On the other hand, emission of active ions from tourmaline particles is increased as the particle diameter of the particles is decreased.

As is well known, the cellulose moiety in the spinning solution of rayon fibers is in the form of a polymeric electrolyte not only in the viscose process but also in the cuprammonium process so that, quite unexpectedly, very uniform dispersion of tourmaline particles can be obtained presumably due to the ionic interaction between the tourmaline particles and the polymeric electrolyte even when the particle diameter of the tourmaline particles is extremely small.

Tourmaline, which is dispersed in the rayon-based fibers in the form of fine particles, is a kind of naturally occurring minerals and has a chemical composition expressed by the general formula

$$MX_3B_3Al_3(AlSi_2O_9)_3 (O,OH,F)_4,$$

in which M is an atom of sodium or calcium and X is an atom of aluminum, iron, lithium, magnesium or manganese. Tourmaline of high purity having good transparency is known as a gem stone and methods for the preparation of artificial single crystals of tourmaline have been developed. In the present invention, the origin of the tourmaline is not particularly limitative and natural and artificial tourmaline crystals can be used equally. Tourmaline is susceptible to spontaneous permanent electric polarization without influences on the vector of polarization by an external electric field. The permanent polarization of tourmaline is the strongest among minerals. It is also known that tourmaline emits far infrared light. Further, tourmaline is susceptible to the piezo-electric effect which is a phenomenon that a dielectric polarization is induced in an ionic crystal under application of a stress by an external force and also susceptible to the pyroelectric effect which is a phenomenon of appearance of electric charges on the surface of the crystal when the crystal is locally heated. It is also an established fact that anionic active ions are emitted from fibers containing fine particles of tourmaline dispersed therein.

The effect of active ion emission from tourmaline is greatly enhanced when the mineral is in the form of extremely fine particles. In this regard, the tourmaline particles used in the invention should have a particle diameter not exceeding 0.3 $\mu$m or, preferably, not exceeding 0.2 $\mu$m with an average particle diameter not exceeding 0.15 $\mu$m. The amount of the tourmaline particles contained in the rayon fibers is in the range from 0.05 to 2.0% by weight or, preferably, from 0.05 to 1.0% by weight based on the amount of the rayon from the standpoint of obtaining a good balance between the active ion emission and the cost. When the amount of the tourmaline particles is too small, active ion emission would be too low as a matter of course while an increase in the amount of the tourmaline particles to exceed the above mentioned upper limit has no particular additional advantages rather with an economical disadvantage due to an increase in the costs.

It is optional that the tourmaline-containing rayon fiber of the invention further contains fine particles of other inorganic or ceramic materials emitting far infrared light including alumina, silicate minerals such as cordierite and β-spodumene, zirconia, zircon, magnesia, aluminum titanate and the like as well as transition metal compounds such as manganese dioxide, iron oxide, chromium oxide, cobalt oxide and copper oxide, silicon nitride, silicon carbide and the like.

DESCRIPTION OF THE PREFERRED EMBODIMENTS

The following is a description of a preferred embodiment of the method for the preparation of the inventive tourmaline-containing rayon fiber, taking the rayon fibers by the so-called viscose process as an example.

In the first place, tourmaline mineral is finely pulverized into particles having a particle diameter not exceeding 0.3 $\mu$m or, preferably, not exceeding 0.2 $\mu$m. The method for the pulverization of tourmaline is not particularly limitative including dry-process and wet-process methods, of which the wet-process method by using water as the medium is preferred in respect of the efficiency. If desired, one or more of optional inorganic or ceramic materials mentioned above can be pulverized together with tourmaline in the wet-process pulverization procedure. The thus obtained tourmaline particles are added to an aqueous spinning solution of rayon by the viscose process in a specified amount to give an aqueous spinning solution of viscose rayon containing the tourmaline particles which is subjected to spinning in a conventional manner. It is optional that the spinning solution is admixed with an antibacterial agent, antifungal agent, deodorant and the like according to need.

The efficiency of active ion emission from the tourmaline-containing rayon fibers can be estimated by the testing procedure describer later, in which the active ions emitted from the tourmaline-containing rayon fibers are carried off by the flow of an inert carrier gas and continuously introduced into distilled water of which the electric conductivity is monitored to detect an increase in time corresponding to the active ion emission from the fibers. For example, the living body invigorating effect by the tourmaline-containing rayon fibers is particularly remarkable when the conductivity of the distilled water is at least 2.2 $\mu$S/cm at a moment after 3 hours from start of the test.

In the following, description is given to illustrate the tourmaline-containing rayon fibers and the method for the preparation thereof in more detail by way of examples although the scope of the present invention is never limited thereby in any way.

EXAMPLE 1

Tourmaline-containing rayon fibers were prepared in the following manner.

According to the conventional procedure, an alkali cellulose was prepared from 100 parts by weight of wood pulp which was agitated at room temperature for 2 hours with addition of 350 parts by weight of a 20% by weight aqueous solution of sodium hydroxide. The alkali cellulose was admixed with 30 parts by weight of carbon disulfide and agitated at room temperature for 3 hours to give a solution of a sodium cellulose xanthate.

In the next place, the above prepared xanthate solution was diluted by the addition of an aqueous solution of sodium hydroxide to give a spinning solution containing 8.7% by weight of cellulose, 6.0% by weight of total alkali and 2.4% by weight of total sulfur. The spinning solution was admixed with fine particles of tourmaline having a particle diameter not exceeding 0.2 $\mu$m and an average particle diameter of 0.15 $\mu$m obtained by the method of water-granulation in amounts of 0.05%, 0.1%, 0.2%, 0.3%, 0.5%, 1.0%, 2.0%, 3.0%, 5.0% and 7.0% by weight based on the cellulose content.

The spinning solution containing tourmaline particles was subjected to spinning into a spinning bath at 50° C. containing 120 g/liter of sulfuric acid, 280 g/liter of sodium sulfate and 15 g/liter of zinc sulfate at a spinning velocity of 60 meters/minutes through a spinnerette having 50 holes of 0.08 mm diameter followed by stretching in a conventional two-bath stretch spinning method to give tourmaline-containing rayon fibers in different contents as above, referred to as the fibers No. 1 to No. 10, respectively, having fineness of 15 denier.

The rayon fibers containing different amounts of the tourmaline particles were subjected to the test for the estimation of active ion emission in the following manner.

Emission of active ions from the tourmaline-containing rayon fibers was investigated by means of the changes in the electric conductivity of water blown with air after passing through a bed of 20 g of the tourmaline-containing rayon fibers by using the apparatus system schematically illustrated in FIG. 1 in a procedure described below. The sample of tourmaline-containing rayon fibers prepared as above was mounted on the sample mount 3 installed inside of the activation vessel 2. The blower pump 1 was operated to introduce clean air freed from carbon dioxide and the like into the activation vessel 2 at a rate of 100 ml/minute while keeping the sample fibers on the sample mount 3 at a temperature of 35° C. by means of a ceramic heater 4 under power supply from the power source 7 and surrounding the activation vessel 2 which was equipped with a thermometer 5 and a temperature sensor 6 to facilitate temperature control.

The air permeating the sample mount 3 was blown at the surface of the distilled water 10 at 21° C., of which the initial conductivity was 1.7 $\mu$S/cm at 21° C., in a glass beaker 9 held in a thermostat 8. The change in the conductivity of the water 10 was monitored with a conductivity meter 12 (Precision LCR Meter, Model 4285A, manufactured by Hewlett-Packard Co.) by means of the rod-formed platinum electrodes 11 inserted into the water 10. Table 1 below gives the value of the conductivity of the distilled water 10 after three hours of continued blowing of the air at the surface of water for the fiber samples No. 1 to No. 10 containing varied amounts of the tourmaline particles having a particle diameter not exceeding 0.2 $\mu$m in the range from 0.05% to 7.0% by weight. The conductivity of the water after three hours of air blowing in the above described manner is graphically shown as a function of the content of the tourmaline particles in the rayon fibers by the curve A of FIG. 2.

EXAMPLE 2

The experimental procedure was substantially the same as in Example 1 except that the tourmaline particles incorporated into the rayon fibers had a particle diameter not exceeding 1.0 $\mu$m with an average particle diameter of 0.8 $\mu$m in place of the finer tourmaline particles used in Example 1. The values of the conductivity of the distilled water after three hours of air blowing are shown for the samples No. 11 to No. 21 containing varied amounts of the tourmaline particles, sample No. 11 being for the purpose of control with the rayon fibers containing no tourmaline particles. The conductivity of the water after three hours of air blowing is graphically shown as a function of the content of the tourmaline particles in the rayon fibers by the curve B (broken line curve) of FIG. 2.

TABLE 1

| | | Example 1 | | Example 2 | |
|---|---|---|---|---|---|
| | | Fiber sample No. | Conductivity, $\mu$S/cm | Fiber sample No. | Conductivity, $\mu$S/cm |
| Content | 0 | — | — | 11 | 1.84 |
| of | 0.05 | 1 | 2.24 | 12 | 2.10 |
| tourmaline | 0.1 | 2 | 2.39 | 13 | 2.15 |
| particles, | 0.2 | 3 | 2.42 | 14 | 2.17 |
| % by | 0.3 | 4 | 2.42 | 15 | 2.16 |
| weight | 0.5 | 5 | 2.34 | 16 | 2.13 |
| | 1.0 | 6 | 2.28 | 17 | 2.13 |
| | 2.0 | 7 | 2.19 | 18 | 2.11 |
| | 3.0 | 8 | 2.15 | 19 | 2.08 |
| | 5.0 | 9 | 2.10 | 20 | 2.10 |
| | 7.0 | 10 | 2.06 | 21 | 2.08 |

As is understood from these experimental results, the electric conductivity of the distilled water was increased to 2.08 to 2.17 $\mu$S/cm after three hours of air blowing at the surface of water when the air was passed through a bed of the tourmaline-containing rayon fibers, of which the tourmaline particles had a particle diameter not exceeding 1.0 $\mu$m, as compared with the control with rayon fibers containing no tourmaline particles giving a conductivity of water of 1.84 $\mu$S/cm. The electric conductivity of the distilled water was little dependent on the content of the tourmaline particles in the rayon fibers when the tourmaline content was in the range from 0.05 to 2.0% by weight.

When the tourmaline particles incorporated into the rayon fibers had a particle diameter not exceeding 0.2 $\mu$m (Example 1, curve A of FIG. 2), on the other hand, the electric conductivity of the distilled water had a maximum value at a tourmaline content of 0.2 to 0.3% by weight and decreased when the tourmaline content was further increased up to 2.0% by weight. The electric conductivity of the distilled water was much higher than in Example 2 indicating that the active ion emission greatly depends on the particle diameter of the tourmaline particles.

Figure 2:
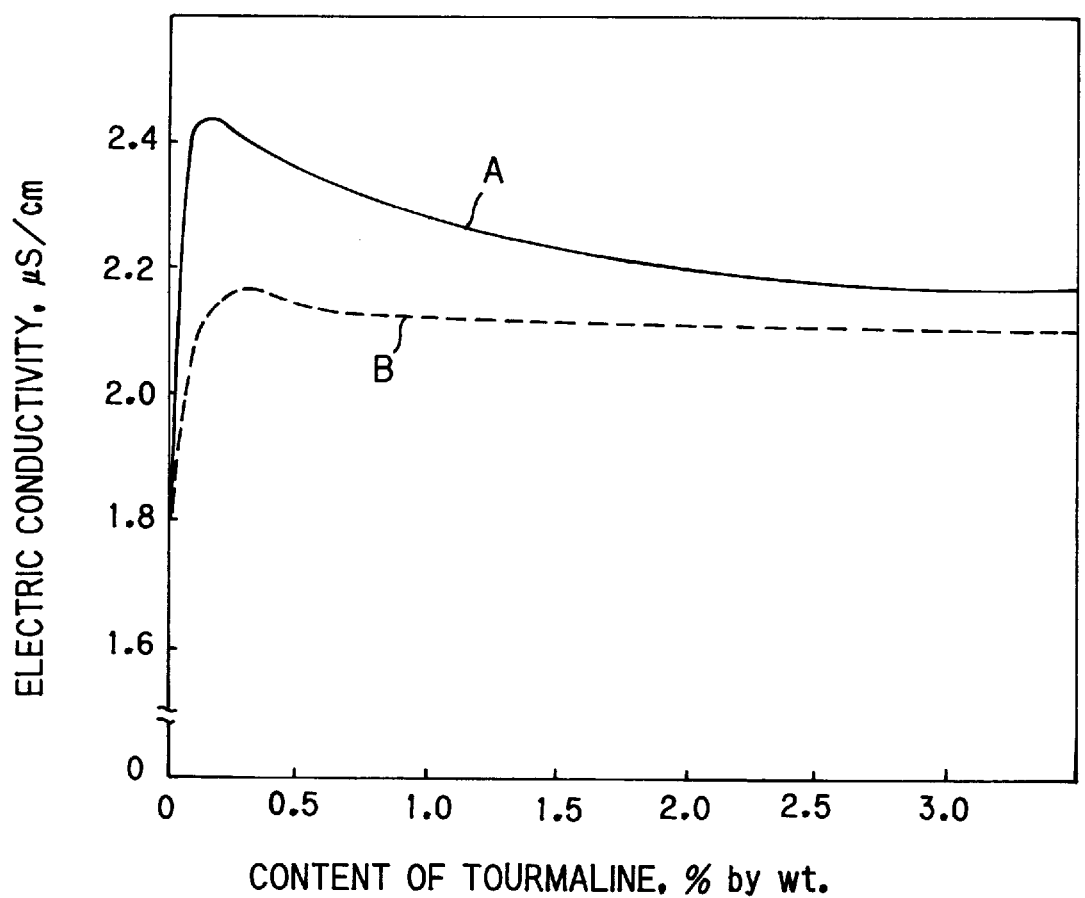
FIG. 2 is a graph showing the electric conductivity of the water capturing the active ions emitted from the electret fibers prepared in the Examples by using the apparatus system shown in FIG. 1 as a function of the content of tourmaline particles in the fibers.

Further, the sample fibers No. 3 and No. 9 prepared in Example 1 containing 0.2% by weight and 5.0% by weight, respectively, of the tourmaline particles were each subjected to the examination with a high-resolution transmission electron microscope (Model JEM-200CX, manufactured by Nippon Denshi Co.) at an electron acceleration voltage of 160 kV to find that the tourmaline particles in sample No. 3 had a particle diameter in the range from 0.02 to 0.2 $\mu$m ranging mostly at 0.1 $\mu$m or smaller and were dispersed in the fibers uniformly and discretely while the particles in sample No. 9 were in the form of agglomerates of primary particles of a diameter not exceeding 0.1 $\mu$m, the agglomerates mostly having a diameter in the range from 0.2 to 1.8 $\mu$m. These results of the electron microscopic examination indicates that, when the tourmaline content in the fibers was low, the tourmaline particles can be very uniformly dispersed in the fibers but, when the tourmaline content is too high, the particles form agglomerates as a trend. These results are in good consistency with the curve A in FIG. 2 showing a great increase in the electric conductivity of the distilled water in the range of the tourmaline content from 0.05 to 2.0% by weight.

Application Example. (Thermographic skin-thermometry)

The thermographic skin-thermometry is a method in which the skin temperature is measured with an infrared camera of ultra-high sensitivity and the distribution of the skin temperature is expressed in a chart called a thermogram by using 10 different colors corresponding to the respective temperature ranges.

Three mattresses for bed sheeting, referred to as the mattresses A, B and C, were prepared from different rayon fibers including the tourmaline-containing rayon fibers of sample No. 3 prepared and tested in Example 1, the tourmaline-containing rayon fibers of sample No. 14 prepared and tested in Example 2 and rayon fibers of sample No. 11 containing no tourmaline particles, respectively. Each of the mattresses A, B and C was spread on a bed and a healthy adult person as a subject was kept lying thereon with his face facing upwardly. The skin temperature of the subjects was monitored by the thermography to find that the temperature of their feet was increased by 1.1° C. and by 0.6° C. on the mattresses A and B, respectively, during and after lying indicating invigoration of the subcutaneous blood circulation while almost no temperature increase was detected on the feet of the subject lying on the mattress C.

The above described experimental results lead to a conclusion that the tourmaline particles contained in the rayon fibers have an effect to increase the temperature of human skin by the invigorating effect on the subcutaneous blood circulation and this effect depends on the particle size of the tourmaline particles in good coincidence with the results by the measurement of electric conductivity of water obtained in Examples 1 and 2. In other words, measurement of the conductivity of water conducted in Examples 1 and 2 would provide good indices on the invigorating activity of the tourmaline-containing rayon fibers on the living body cells to cause promotion of the subcutaneous blood circulation.

What is claimed is:

1. A fiber of rayon containing particles of tourmaline having a maximum particle diameter of 0.2 μm and an average particle diameter not exceeding 0.15 μm. and in which the amount of the particles of tourmaline is in the range from 0.05 to 2.0% by weight based on the amount of the unloaded rayon fiber.

2. The fiber of rayon as claimed in claim 1 in which the amount of the particles of tourmaline in the range from 0.05 to 0.5% by weight based on the amount of the unloaded rayon fiber.

3. The fiber of rayon as claimed in claim 1 which further contains, in addition to tourmaline, fine particles of other inorganic materials which emit far infrared light.

4. The fiber of rayon according to claim 3, wherein such inorganic materials comprise ceramic materials.

5. The fiber of rayon according to claim 3, wherein the inorganic materials comprise alumina.

6. The fiber of rayon according to claim 3, wherein the inorganic materials comprise silicate minerals.

7. The fiber of rayon according to claim 6, wherein the silicate materials are cordierite or β-spodumene.

8. The fiber of rayon according to claim 3, wherein the inorganic materials comprise transition metal compounds.

9. The fiber of rayon according to claim 8, wherein the transition metal compounds are selected from the group consisting of manganese dioxide, iron oxide, chromium oxide, cobalt oxide and copper oxide.

10. The fiber of rayon according to claim 3, wherein the inorganic materials comprise silicon nitride or silicon carbide.

11. The fiber of rayon according to claim 3, wherein the inorganic materials comprise zirconia, zircon, magnesia or aluminum titanate.

* * * * *